United States Patent [19]
Bowen et al.

[11] Patent Number: 4,802,761
[45] Date of Patent: Feb. 7, 1989

[54] OPTICAL-FIBER RAMAN SPECTROSCOPY USED FOR REMOTE IN-SITU ENVIRONMENTAL ANALYSIS

[75] Inventors: John M. Bowen; Patrick J. Sullivan; M. Sterling Blanche; Michael Essington; Lewis J. Noe, all of Laramie, Wyo.

[73] Assignee: Western Research Institute, Laramie, Wyo.

[21] Appl. No.: 93,093

[22] Filed: Aug. 31, 1987

[51] Int. Cl.$^4$ .......................... G01J 3/44; G01N 1/10
[52] U.S. Cl. ...................... 356/301; 356/246
[58] Field of Search ................ 356/301, 244, 246

[56] References Cited

U.S. PATENT DOCUMENTS

| | | | |
|---|---|---|---|
| 3,556,659 | 1/1971 | Hawes | 356/301 |
| 3,768,908 | 10/1973 | Zaromb | 356/301 X |
| 3,770,350 | 11/1973 | Stone et al. | 356/301 |
| 3,906,241 | 9/1975 | Thompson | 356/301 |
| 4,012,147 | 3/1977 | Walrafen | 356/301 |
| 4,040,749 | 8/1977 | David et al. | 250/227 X |
| 4,288,161 | 9/1981 | Fortescue | 356/73 |
| 4,573,761 | 3/1986 | McLachlan et al. | 356/301 |
| 4,582,809 | 4/1986 | Block et al. | 250/227 X |
| 4,603,923 | 8/1986 | Döppling et al. | 384/7 |

OTHER PUBLICATIONS

*Analytical Chemistry*, vol. 55, No. 1, Jan. 1983.
Reviews of Modern Physics, vol. 58, No. 2, Apr. 1986.
"Investigation of the Use of the Resonance Raman Effect as an Environmental Monitor", Chamberlain et al., NTIS Report No.: LBL-5288; NSF-RA-760383 Oct. 1976, 65 pages.

*Primary Examiner*—F. L. Evans
*Attorney, Agent, or Firm*—Browdy & Neimark

[57] ABSTRACT

Method and apparatus are provided for remote in-situ detection and/or monitoring of selected compounds in liquid or gaseous media using one of several methods of Raman spectroscopy. The resulting Raman signal is conducted through optical fibers for recording a Raman spectrum at a distance from the instrument.

17 Claims, 1 Drawing Sheet

OPTICAL-FIBER RAMAN SPECTROSCOPY USED FOR REMOTE IN-SITU ENVIRONMENTAL ANALYSIS

BACKGROUND OF THE INVENTION

At present, there is a great need to identify and trace chemical contaminants, especially organic compounds, as they move through the environment. The monitoring of contaminants in ground water is of particular concern because of the difficulty of real time, in situ analysis that not only indicates the presence of, but can quantitate and identify contaminants and their products produced in situ. Further, there exists a need for real time monitoring of contaminants in the atmosphere. It would be convenient to have a monitoring system that is local to the site to be monitored but which can be read at a distance convenient to those regulating these contaminant emissions.

The Raman effects, including RRS, SERS, and SERRS, are well known in the scientific literature, particularly as described in Grasselli et al., *Chemical Applications of Raman Spectroscopy*, Wiley-Interscience, John Wiley and Sons, New York, 1981. The details of Raman spectroscopy are discussed in U.S. Pat. No. 3,556,659, which includes further references on Raman theory.

A number of devices exist that can be used for Raman spectroscopy. McLaughlan et al., in U.S. Pat. No. 4,573,761, disclose a fiber optic probe for Raman analysis comprising a bundle of optical fibers grouped such that at least one optical fiber is used exclusively for transmitting light into the sample while at least two optical fibers arranged at an advantageous angle with the transmitting fiber are used exclusively for collecting light from the sample.

Johnson et al., in *J. Am. Chem. Soc.*, (1986) 108, 905-912, describe the use of ultraviolet resonance Raman techniques to characterize the photoionization products of phenol, tyrosine, and tryptophan.

Marley et al, (1985) *Appl. Spectrosc.* 39, 628-633, and (1984) *Appl. Spectrosc.* 38, 540-543, describe the use of Raman spectroscopy for trace analysis of phenols in water.

A major difficulty associated with Raman spectroscopy is the low intensity of the scattered light compared to the exciting light. Elaborate spectrometers, having high light gathering power and dispersion, high stray light rejection, and sensitive detector, are required to isolate and measure the low intensity Raman scattered light. These instruments are costly and sensitive, and thus are not well suited for use in commercial manufacturing or processing facilities. As a result, they have rarely been used outside of laboratory environments.

Another problem associated with Raman spectroscopy is that of fluorescence, which competes with the Raman effect. Many compounds, including natural products and minerals, fluoresce or emit light when exposed to laser light in the visible region, which further interferes with the Raman signal in samples. Fluorescence bands are usually broad, and are often featureless. Although fluorescence bands are often successfully used for quantitation and sensitive indication that a fluorescing compound is present, fluorescence bands do not provide the unambiguous fingerprinting quality of the Raman spectra. Because of its very nature, the Raman spectrometer also acts as a very sensitive fluorescence spectrometer, and as such, the Raman signal can be buried in the fluorescence.

Another disadvantage of Raman spectra is that, if there are several chemical compounds present in a mixture to be analyzed, all of the compounds will contribute a Raman signal. The resultant Raman spectrum will be an addition of all of the Raman spectra of all of the components in the mixture, and thus very complicated and potentially confusing.

A variety of applications of optical fibers to spectroscopic problems have been described in the past, with particular emphasis on UV-visible absorption and fluorescence techniques. Optical fiber-based sampling devices allow the sample to be remote from the spectrometer. While infrared absorption spectrometry can provide structural information, it is not amenable to fiber optic probes because of poor transmission of infrared light by glass or plastic fibers. Since Raman scattering spectrometry normally uses visible light which is efficiently transmitted by optical fibers, it can provide vibrational information about the sample yet still be easily coupled to a fiber optic probe.

Rong et al., in *Anal. Chem.* (1986), 58, 1116-1119, describe the use of colloidal silver sols for surface-enhanced Raman scattering.

Johnson et al., in *Anal. Chem.* (1984), 56, 2258-2261, disclose that ultraviolet resonance Raman spectroscopy could be used to detect polycylic aromatic hydrocarbons such as naphthalene, anthracene, and pyrene in solvents such as water and acetonitrile. Laser excited resonance Raman spectroscopy has been reported by Van Haverbeke et al. in *Anal. Chem.* 1979, 57, 932-936.

Chamberlain et al., in an NSF Report NSF-RA-760393 disclose that the use of a laser to measure the Raman spectra of molecular constituents remotely can be used to monitor gaseous pollutants.

Enlow et al., in *Anal. Chem.* (1986), 58, 1119-1123, disclose a method for detecting nitro polynuclear aromatic compounds by surface-enhanced Raman spectrometry. The substrates used were silver-coated substrates consisting of latex spheres on glass and filter paper, and prolate silicon dioxide posts on quartz.

There has been some activity in remote detection techniques using optical fibers to carry the Raman spectra to remote sites for detection and evaluation. For example, Chudyk et al., in *Anal. Chem.* (1985), 57, 1237-1242, describe a method of detecting groundwater contaminants using far-ultraviolet laser-induced fluorescence. Schwab et al., in *Anal. Chem.* (1984), 56, 2199-2204, disclose a fiber optic Raman probe wherein both the exciting laser light and the collected Raman scattering are conducted by optical fibers. Nguyen et al., in *Analysis*, (1986), vol. 14, No. 7, 334-343, disclose a method for selective cartography using Raman spectroscopy using optical fibers for remote and in situ analysis. Walragen et al., in *Applied Spectroscopy*, (1972), 26, 585-589, and Ross et al., in *Applied Spectroscopy*, (1981), 35, 438-442, disclose that Raman spectra can be intensified by using liquid core optical fibers.

Schwab et al., in *Applied Spectroscopy*, (1987), 41, 126-130, disclose a long path Raman cell (LPRC) for high sensitivity Raman spectroscopy.

SUMMARY OF THE INVENTION

It is an object of the present invention to overcome the above-mentioned deficiencies in the prior art.

It is a further object of the present invention to provide a method and apparatus for remotely monitoring the presence of selected compounds in either liquid or gaseous media.

It is yet another object of the present invention to provide a method and apparatus for monitoring the presence of and reactions of pollutants in groundwater.

The present invention involves the conduction of Raman spectroscopy through optical fibers, which method has been found to be useful for recording a Raman spectrum at some distance from the instrument.

The present invention provides a method and apparatus for analyzing for selected components in liquid or gaseous media using several methods of Raman spectroscopy, such as Raman scattering (RS), resonance Raman scattering (RRS), and surface-enhanced Raman and surface-enhanced resonance Raman spectroscopy (SERS and SERRS, respectively). In this method, the wavelength of the exciting laser line is carefully chosen to coincide with a wavelength at which light is absorbed by a chemical compound. The Raman spectrum is conducted through optical fibers for recording a Raman spectrum at a distance from the instrument and which can be used to produce an array of sensors capable of not only detecting but also of quantifying chemical compounds at a remote site.

The most challenging problem involved with Raman spectroscopy is that of fluorescence. If a fluorescence band is encountered, the laser line used can simply be moved, or "tuned", given a tunable laser, to a different wavelength, leaving the fluorescence band behind. Further, the fluorescence bands of most chemical compounds are in the visible region of the spectrum. If a laser which emits light in the ultraviolet or the near infrared regions of the spectrum is used for Raman and resonance Raman spectroscopy, little fluorescence is encountered.

For the problem of the faint Raman signal, there are several methods which can be used according to the present invention to boost the Raman signal level up to sometimes a million times the original signal. These methods include:

1. Surface enhanced Raman spectroscopy (SERS);
2. Surface enhanced resonance Raman spectroscopy (SERRS); and
3. Resonance Raman spectroscopy (RRS).

Surface enhanced Raman spectroscopy uses a phenomenon associated with chemical compounds in intimate contact with a specially prepared silver surface.

In resonance Raman spectroscopy, the wavelength of the exciting laser line is carefully chosen to coincide with a wavelength at which light is absorbed by a chemical compound. If the laser wavelength for a Raman spectrum is so situated, the Raman signal that results can be very intense. More importantly, only the Raman spectrum of the compound which has one of its absorption bands thus matched by the wavelength of the laser will be magnified by this effect. If that compound is part of a mixture, the other components of the mixture will exhibit regular sized Raman spectra, but these will be much less intense that the Resonance Raman spectrum, and may not interfere with it. Further, if the wavelength of the laser line is sequentially tuned into the absorption bands of the compounds in the mixture, their Raman spectra will be sequentially and individually enhanced. Any aqueous mixture of compounds could be sequentially analyzed using this procedure.

In the present invention, fiberoptic resonance Raman spectroscopy and fiberoptic SERS and SERRS have been developed and can be used to produce an array of sensors capable of not only detecting individually or together (en masse) as a topographic method, but of identifying chemical compounds of environmental interest in a number of environments, including groundwater, smokestack emissions, surrounding a pipeline carrying hazardous materials, and the like.

A tunable laser is used to "tune" the laser wavelength away from the fluorescence band so that the Raman spectrum is no longer interfered with.

Alternatively, a mixture of chemical compounds will produce a mixture of Raman spectra. Given a Raman spectral library of likely compounds, computer programs can be modified to "deconvolute" or identify each component by its band pattern.

The resonance method is useful in overcoming the lack of signal intensity inherent in Raman spectroscopy by boosting the signal intensity to high levels. This method increases the signal intensity of the Raman spectrum of a given chemical compound when the laser wavelength is tuned into the electronic absorption envelope of that compound.

Given a mixture of chemical compounds that have electronic absorption bands sufficiently separated from each other, and a laser that can be tuned into each absorption band sequentially, the resonance Raman spectrum of each compound will be enhanced sequentially. This enables one to analyze a mixture of compounds without chemical separation thereof.

In another application using SERS and SERRS, electrochemically roughened metal electrodes in a specialized cell or a cell constructed of semipermeable glass containing a metal sol (colloidal suspension), are used as environmental monitors for ground water contaminants. In this method, the laser wavelength can be tuned into not only the electronic absorption bands of the absorbate (chemical contaminant), but may also be tuned into the plasmon-resonance band of the adsorbate-metal complex. Both of these effects produce increases in sensitivity as well as selectivity.

In yet another application using RRS, the optical fiber probe is used as a short range LIDAR device for the detection and analysis of gas phase compounds of environmental interest.

The process of the present invention is used for remote in situ analysis of an aqueous phase in a natural environment such as groundwater, surface water, saturated soil water, unsaturated soil water; industrialized processes such as waste water, cooling water; chemicals used in a process, chemical reactions in an industrial processes, and other disturbed systems that would include leachate from waste sites; waste and water injection processes; liquids in or leak detection around storage tanks; discharge water from industrial facilities, water treatment plants or facilities; drainage and leachates from agricultural lands, drainage from urban land uses such as surface, subsurface, and sewer systems; waters from waste treatment technologies; and drainage from mineral extraction or other processes that extract natural resources such as oil production and in situ energy production. The techniques of the present invention can be used for in situ monitoring of microbial transformation of chemical compounds.

DETAILED DESCRIPTION OF THE INVENTION

Figure 1:
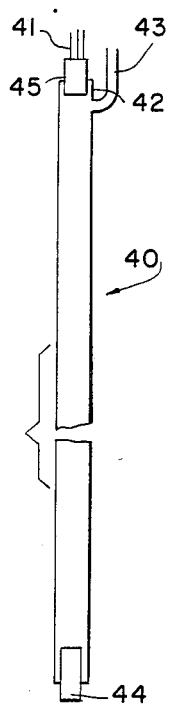
FIG. 1 shows a schematic of a Raman ground water cell configured for RS, RRS, SERS, and SERRS.

The instrument which is particularly suited for use in the present invention requires a fast monochromator, or Fourier Transform interferometer coupled with the appropriate lenses to the collection end of an optical fiber or bundle of optical fibers similar to that described in U.S. Pat. No. 4,573,761, and which is hereby incorporated herein by reference. For a single optical fiber system, a mirror with a small perforation through which the excitation light is focused onto the fiber end can be used. The rest of the mirror then collects all but a fraction of the Raman radiation returning through the fiber and directs it to the monochromator. For a multiple fiber bundle system, light from the excitation source is focused onto the end of the transmission or central optical fiber, while the Raman radiation is collected by the surrounding array of collection fibers. These collection fibers are then directed to the coupling lenses and then to the monochromator.

The preferred embodiment of the invention utilizes a pulsed laser that is tuneable from 220 nm to 900 nm. The detection system is based on an image intensified diode array detector, with gated electronics, which is coupled to a computer which records the data and controls the instrument.

For some applications of in situ environmental analysis using optical fibers, a specialized instrument can be constructed that incorporates only a few of the components of the instrument herein described. The instrument herein described in detail is the presently preferred embodiment. An example of such a simplified device includes a simple spectrometer set to a specific wavelength coupled with a non-tuneable laser such as a diode laser, or even an intense non-laser source.

The present invention takes advantage of the several methods of enhanced Raman spectroscopy in order to alleviate the inherently weak nature of Raman scattered light. These methods include resonance Raman spectroscopy (RRS), surface enhanced Raman spectroscopy (SERS), and a combination of the two, surface enhanced resonance Raman spectroscopy (SERRS). These methods take advantage of the enhancement of the Raman signal which can be as great as six orders of magnitude, making this method viable as an environmental monitor.

The mechanism of RRS is well known. Its origin is based on the pronounced enhancement of scattering from allowed vibrational modes in an excited electronic state that occurs when the exciting laser frequency becomes resonant with the electronic transition. To effectively take advantage of the RRS phenomenon for the purpose of environmental measurements, a laser that is tuneable is required. The method involves tuning the laser excitation wavelength into an electronic absorption band of the analyte. This method allows for some ability to distinguish among the individual components in a complex mixture.

If the wavelength of the excitation light is tuned through the absorption envelopes of a mixture of compounds one at a time, the spectra of each compound in turn will be enhanced over the others by the RRS effect to the ability of the instrument to differentiate between absorption envelopes. The resonance spectrum is then recorded in the normal way.

SERS, on the other hand, is not so well understood. The effect is associated with three characteristics. These characteristics include the use of a metal such as silver, copper, lithium, potassium, iridium, rhenium, or platinum, the surface of which is roughened such that metal particles on the size and scale of a colloid are present, and the excitation energy must be below the "interband threshold" for the metal substrate. The SERS effect can be made even more useful by probing an absorption band of an adsorbate. This utilizes the advantage of the SERS effect and the RRS effect to cause an enhancement that is made up of a combination of the two effects, and is called the SERRS effect. This effect has the same advantages of differentiation as the RRS effect.

In situ analysis herein is defined as any analysis wherein the apparatus that determines the concentration of an organic or inorganic substance in contact with the liquid or gaseous phase being analyzed is connected to the analyte through optical fibers, or the apparatus that determines the concentration of an organic or inorganic substance is not in physical contact with the liquid or gaseous phase that is being analyzed.

According to the present invention, liquid or gaseous phases are analyzed for substances of interest using Raman and resonance Raman spectroscopy and optical fibers to carry the Raman signals to a remote sensing device. Of particular interest is the use of surface enhanced Raman spectroscopy using optical fibers to carry the signals.

A tuneable laser is used to enhance the Raman, resonance Raman spectra or SERS or SERRS of each chemical substance in a mixture of components as each substance is being analyzed. The excitation wavelength is changed to correspond to the absorption envelope or plasmon-resonance envelope of the substance in question.

Optical fibers are used for Raman and resonance Raman analysis of liquids on solid phases.

Algorithms are provided to store and collect spectra and to produce chemical identification and qualitative and quantitative concentrations from any of the types of apparatus used for in situ analysis.

The Raman and resonance Raman spectroscopy is used with optical fibers in combination with a chromatographic prefilter prior to intake of the sample cells or surface enhanced Raman spectroscopy. The chromatographic prefilter is used for gross separation by chemical properties, such as acids from bases, to facilitate the analysis of complex mixtures.

Detection of inorganic or organic pollutants in groundwater is accomplished with the use of surface enhanced Raman and surface enhanced resonance Raman spectroscopy, in combination with optical fibers for carrying the sensing information to a remote reader.

A secondary chemical reaction can be conducted in the mixture of interest to enhance the Raman or resonance Raman spectra of the substances to be detected, and optical fibers are used to carry the signal to a remote sensing device.

The process and apparatus of the present invention can be used as a short range LIDAR device for in situ analysis of a gaseous phase to detect chemical storage facilities, and chemical spills (e.g., as a result of transportation accidents or industrial facility spills), detection of and quantification of volatile organics from waste, waste treatment facilities, and waste disposal facilities; monitoring gases generated by industrial processes such as chemical processing, energy production, stack emissions, indoor air quality; and emissions from internal combustion engines, such as automobiles, trucks, boats, and aircraft.

According to the present invention, an optical fiber bundle or a single optical fiber can be used in conjunction with a microprocessor-operated switching device that can be used as a short range LIDAR array device for the analysis of gaseous pollutants or an array device for topological monitoring or analysis of groundwater pollutants.

For the present invention, the fiber optic probe is designed to mate directly to a Raman spectrometer. The general optical arrangement is that one fiber carries the laser light to the sample, and a plurality of fibers collect the Raman light. The collection fibers are conveniently arranged in a vertical line at the spectrometer and placed in position normally occupied by a sample capillary. The collector of the spectrometer images the slit-shaped output of the collection fibers on the entrance slit of the monochromator. The output of an argon ion laser is focused onto a single input fiber using the spectrometer's illumination optics. Although this device is the present configuration, the invention is not limited by the details of the design of this device.

The collection fibers and input fibers are made from 200 micron core diameter silica fibers which have a numerical aperture of 0.4. The cladding consists of silica of a differing index of refraction. The buffer is a 15 micron thick layer of a hard fluorocarbon coating which is chemically more resistant than silicone rubber and allows closer packing of the fibers into a bundle. Any optical fiber of any dimension which has suitable transmission characteristics can be used in this device.

The total length of the fibers from the spectrometer to the probe can be as long as is required to separate the probe from the spectrometer. Approximately 75% of the 488-nm laser light incident on the input fiber is transmitted to the sample, with most of the loss occurring during coupling. The light loss in the fibers is about 0.5% per meter, but this value is wavelength-dependent.

The best collection fiber is one with a large numerical aperture and thin cladding; however, the light collection is generally limited by the spectrometer rather than the collection fiber.

The RRS-RS technique is further enhanced by the use of liquid filled waveguides or Long Path Raman Cells (LPRC) which can, by using a longer sample pathlength, increase sensitivity from 50 to 250 times, depending upon the length of the cell.

For liquid samples, the probe end can be immersed in the liquid without regard to positioning except for the distance from the probe end to the bottom of the sample. For further enhancement of up to 250 times per meter, the fiberoptic probe can be coupled to a liquid filled waveguide or liquid filled optical fibers.

In a slightly different configuration, a long path Raman cell can be provided. For use with SERS/SERRS, other sample designs are possible.

Since the fiber probe is remote from the spectrometer, the temperature of the sample does not affect the instrumentation. Thus, the present invention can be used in any type of hostile environment irrespective of the temperature of that environment. The upper limit of the temperature is determined by the material used to bind the fiber probe together, the materials of which the fibers are made, and the like.

Detection techniques based on surface-enhanced Raman scattering (SERS) techniques using silver-coated substrates can also be used in the present invention. A number of observations have recently indicated enhancement in the Raman scattering efficiency by factors of $10^3$ to $10^6$ where a compound is adsorbed onto a roughened metallic surface having submicrometer protrusions. The technique associated with this phenomenon is known as SERS spectrometry.

A number of practical procedures for preparing SERS-active surfaces with well-defined roughness and structures are known in the art.

One of these methods uses filter paper covered with silver-coated submicrometer spheres. Other supports which can be used as solid supports for the microspheres are glass and quartz. Additionally, a SERS-active medium can be based on etched quartz substrates having prolate $SiO_2$ posts coated with silver.

Another method involves the use of metal (silver and others) colloids or sols, open or encapsulated within a semipermeable glass membrane at the end of the optical fiber probe. This device enhances the resultant Raman signal with the SERS or SERRS effect. The SERRS effect is accomplished by varying the laser wavelength, as in RRS into the plasmon-resonance envelope of the organic-metalloid complex.

The process of the present invention can also be used in conjunction with resonance Raman spectrometry. In this method, the wavelength of the exciting laser line is carefully chosen to coincide with a wavelength at which light is absorbed by a chemical compound. The absorption bands that will produce this effect for most chemical compounds occur in the ultraviolet and the visible regions of the spectrum. If the laser wavelength for a Raman spectrum is so situated, the Raman signal that results can be very intense. More importantly, only the Raman spectrum of the chemical compound which has one of its absorption bands thus matched by the wavelength of the laser will be magnified by this effect. If that compound is part of a mixture, the other mixture components will exhibit regular sized Raman spectra, but these will be much less intense than the resonance Raman spectrum, and may not interfere with it. Furthermore, if the wavelength of the laser line is sequentially tuned into the absorption bands of the other compounds in the mixture, their Raman spectra will be sequentially and individually enhanced. Any aqueous mixture of compounds could be sequentially analyzed using this procedure.

In the present invention, sample cells of a design capable of insertion down the shaft of a well, or placement in a remote location, must be used. These cell designs are meant to facilitate the practice of the invention and not to limit the invention to these particular designs.

The designs are based on the optical fiber bundle, and incorporate a 180 degree backscattering geometry. All of the sampling cells described hereinafter incorporate protective sheaths in their final versions.

FIG. 1 shows a cell designed to monitor groundwater contaminants in a well remote from the instrumentation. The cells provide enhancement by increasing the cell pathlength. The cell is up to two meters in length, and ma optionally be mirrored inside. The diameter of the tube is similar to that of the optical fiber or optical fiber bundle. The end of the cell tube is fitted with one or more filters capable of eliminating particulates and/or performing gross chemical separations, such as hydrophobic/hydrophilic separations.

In FIG. 1, the cell is shown at 40. An optical fiber or fiber bundle 41 is located at the top of the tube 42 forming the cell. Sample outflow is from a leg 43 in the tube. The bottom of the tube is open for inflow through a filter 44. A protective cap 45 covers the top of the tube. The entire cell is enclosed in a protective casing for downhole use (not shown).

The laser excitation light from the transmission optical fiber 41 is directed down the cell tube 42 which acts as a light wave guide, The backscattered Raman radiation is then guided by the tube 42 toward the collecting optical fibers 41. At the top of the cell is an outlet 43 which is connected by flexible tubing with the surface to a vacuum line in order to change the observed volume of ground water.

Figure 2:
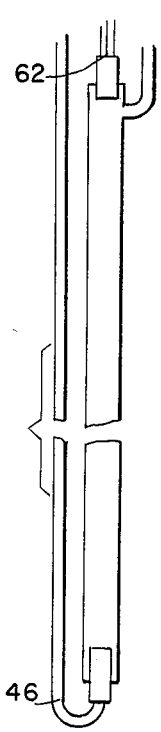
FIG. 2 shows a schematic of a Raman ground water cell as in FIG. 1, with an access tube connected at the inlet end.

A more advanced version of the same cell is shown in FIG. 2, which cell incorporates a tube 46 from the surface that is connected to the inlet filter. This tube can carry cleaning solvents, Raman standards (to ensure calibration), and metal sols to induce the SERS/SERRS effect. The solvents in this tube are separated by bubbles of air, in much the same way as is accomplished in commercial autoanalyzers. Backflow out of a cell inlet filter is blocked by a one way valve.

Figure 3:
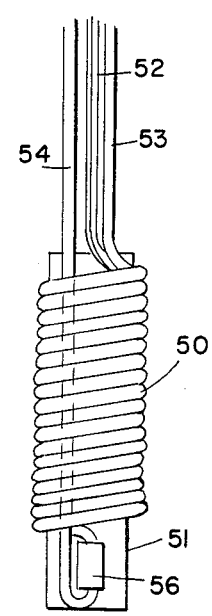
FIG. 3 shows a schematic of a Raman ground water cell as in FIG. 2, using a longer coiled liquid filled waveguide..

In a third version, shown in FIG. 3, the cell 50 is coiled around a support 51. This enables the cell, a liquid filled waveguide related to that shown in U.S. Pat. No. 3,770,350, to be up to 20 meters in length. The inside of the tube can optionally be mirrored. The optical fiber or fiber bundle is shown at 52, and the sample outflow to a vacuum at the surface is shown at 53. An access tube is provided to inject cleaning fluid and/or a metal sol. The advantage of the long length is the enhancement of the signal provided by the greater number of analyte molecules in the light path. This version also incorporates an outlet tube 53 to the surface vacuum line, and the reference inlet tube 54 at the inlet filter end 56. This tube permits cleaning fluids, standard samples, and metal sols to be injected into the sample cell. These liquids can be separated by bubbles of air in the tube, which allows the tube to be cleaned and for SERS/SERRS to be run in addition to RRS.

Figure 4:
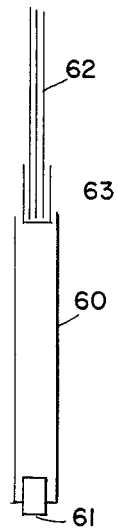
FIG. 4 shows a SERS/SERRS ground water cell designed to incorporate metal sols.

The next three cell designs are for use exclusively with the SERS/SERRS system. The most simple device is shown in FIG. 4, which incorporates a semipermeable glass cylinder 60 plugged at one end by a glass stopper 61, and sealed to an optical fiber or optical fiber bundle 62 at the other. A protective cap 63 at the top of the cell may optionally focus. The cell is filled with a metal sol at a concentration that will permit the transport of organic contaminants. The analytes will then adsorb or become associated with the sol particles which will enable the SERS/SERRS effects to be used.

In this version, a metal sol (colloidal suspension) is sealed in the cylindrical membrane. The concentration of the sol is arranged such that the osmotic pressure encourages transport of organic contaminants into the cell. The organics will adsorb onto the metal sol, and the SERS or SERRS effect can then be used. This cell is inexpensive, is easily fabricated, and is disposable. With SERRS, some spectral separation of the compounds is possible.

Figure 5:
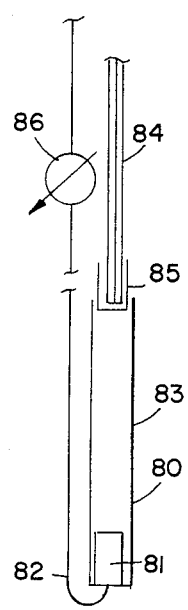
FIG. 5 shows a SERS/SERRS ground water cell incorporating an electrode surface.

Another variation is shown in FIG. 5, wherein the end of the semipermeable glass cylinder or a perforated glass cylinder 80 is sealed to a metal electrode 81 which is connected to the surface by electrical cables 82. The potential of the electrode is designed to be changed remotely, e.g. by a voltage regulator 86. The analyte compounds will pass through the cell body, will become associated with the electrode surface, and will be analyzed by the SERS/SERRS effect. After analysis, the potential of the electrode can be changed to regenerate the electrode surface. A semipermeable membrane 83 allows analyte molecules into the sample cell. The optical fiber or bundle is shown at 84, and the protective cap at 85.

Figure 6:
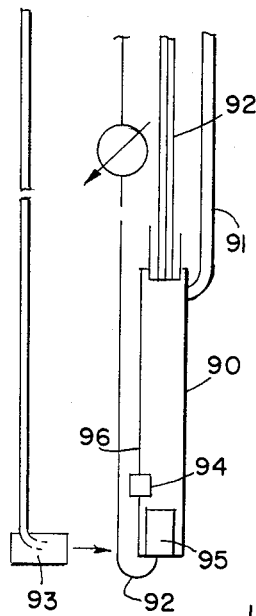
FIG. 6 shows a SERS/SERRS ground water cell as in FIG. 5, incorporating a flow through design.

In yet another variation, shown in FIG. 6, the cell 90 is connected to a surface vacuum line by an outlet 91 near the optical fiber or bundle 92 as in the RRS cell. Further, a filter 93 and one way valve 94 at the electrode 95 end would be connected to the surface by a tube 96 which would carry cleaning solvents and Raman standards as described for the cell in FIG. 2. In this configuration, the sample is pulled into the cell through a one way valve at the electrode by a vacuum. The old sample is pulled out to the surface. The one way sample intake valve may be fitted with a filter to eliminate particles, and in some cases perform gross chemical separations.

Figures 7, 7A:
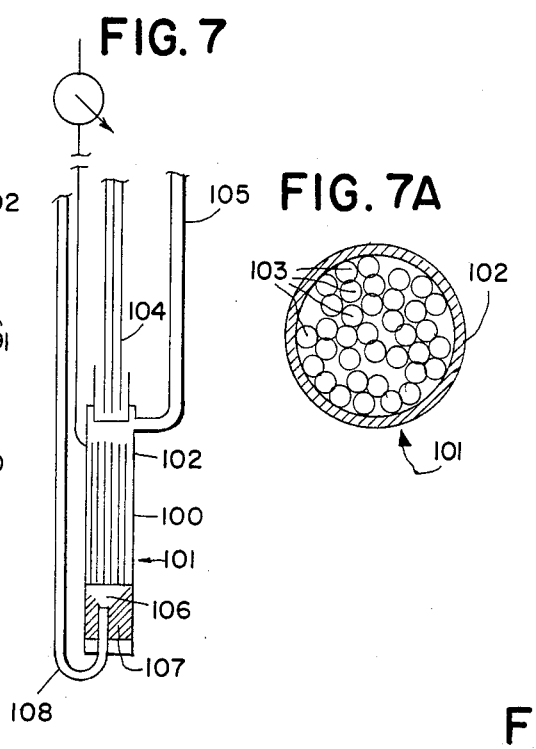
FIGS. 7 and 7A show a RS/RRS ground water cell of flow through design where the cell body itself comprises an electrode.

FIGS. 7 and 7A show a sample cell 100 for the SERS/SERRS effect which comprises only an electrode 101. In this version, the electrode comprises a cylinder 102 made of an appropriate metal such as silver, the interior of which is made up of many small diameter tubes 103 of the same metal, all of which are in electrical contact with each other. The diameter of the outside tube can be similar to the diameter of the optical fiber bundle. The entire electrode interior surface is treated to be appropriate for the SERS/SERRS phenomena. The inner tubules both act to increase the electrode surface area, and as wave guides for the excitation radiation. The electrode is sealed to the optical fiber bundle 104. At that junction, an exit port is connected by a tube 105 to the surface vacuum line. The bottom of the electrode is sealed to a filter 106 coupled to a one way valve 107. The filter is to eliminate particulates and/or to provide gross chemical separation. An access tube 108 penetrates the filter from the surface, through which cleaning solvents or Raman standards can be flushed.

In this version, the sample cell is constructed from a metal of choice. The tubles are made of the same metal as the cylinder. The light from the optical fiber is incident on these tubules. Each tubule acts as a wave guide for both the excitation and SERS/SERRS radiation. The honeycomb interior provides greater surface area for the SERS/SERRS effect. The entire honeycomb electrode is connected to the surface by electrical cables.

The cell also incorporates an outlet to a surface vacuum line, a filter at the entrance to the cell, and an inlet tube from the surface which can be used to flush the cell with cleaning solvent.

Figure 8:
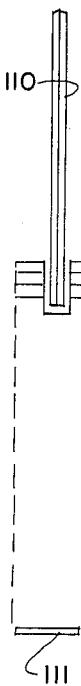
FIG. 8 shows a RS/RRS gas phase cell which can be used as a short range LIDAR device.

FIG. 8 shows an optical fiber or optical fiber bundle 110 situated remotely from the instrumentation to detect toxic gasses using the RRS effect. The instrument works as a short range LIDAR device. The optical fiber transmits laser light of appropriate wavelength to excite the gaseous samples near the end of the optical fiber bundle. The Raman radiation would then be collected by the optical fibers and returned to the instrument. This design may optionally incorporate a nonreflective stop 111 at a given distance from the optical fibers, or a protective hood. This cell can be modified for SERS/SERRS by placing an appropriately prepared metal electrode in front of the optical fiber bundle.

This device can be set up to detect toxic gases in the environment. The optical fibers transmit CW on pulsed laser light, and the Raman or resonance Raman effect is detected through gated electronics (i.e., the instrument will only be turned on when the laser is on, to remove stray light noise). The laser can also be tuned to the absorption bands of the gas being detected.

A plurality of these devices may be provided for topological mapping, or can be used as in-situ detectors or monitors.

The process and apparatus of the present invention can be used for in situ analysis of an aqueous phase in the natural environment (e.g., groundwater, surface water, saturated soil water, unsaturated soil water), industrial processes (e.g., waste water, cooling water, chemical utilized in a chemical process, chemical reactions in an industrial process, chemical products and wastes in an industrial process) and other disturbed systems that would include leachate from waste, either hazardous or nonhazardous, sites, waste and water injection processes, liquids in or lead detection in the vicinity of storage tanks, both aboveground and underground, waste ponds and surface storage, discharge water from industrial facilities, water treatment plants of facilities, drainage from agricultural lands which are idle, under crop production or animal production, drainage from urban land uses, surface, subsurface, or sewer systems. Waters from waste treatment technologies, and drainage from mineral extraction or other processes that extract natural resources, such as oil production and in situ energy production. The process of the present invention can also be used for in situ monitoring of microbial transformation of chemical compounds.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for remote in-situ detection of at least one compound of interest in liquids or gases comprising:
    introducing a collecting cell into the liquid or gas; said collecting cell comprising a tube having a top and a bottom;
    an optical fiber bundle at the top of said tube, a filter at the bottom of said tube, and a protective cap covering said tube;
    obtaining at least one Raman spectrum for the compound of interest in the liquid or gas;
    carrying the Raman signal obtained through optical fibers to a sensing device remote from the site of the liquid or gas; and
    reading the sensing device to detect the presence or amount of the compound of interest.

2. The method of claim 1 wherein the Raman spectrum is a resonance Raman spectrum.

3. The method of claim 1 wherein the Raman spectrum is a surface enhanced Raman spectrum.

4. The method of claim 1 wherein the Raman spectrum is a surface enhanced resonance Raman 5. The method of claim 1 wherein a chromatographic prefilter is used prior to intake to the collecting cell.

6. The method of claim 1 wherein groundwater pollutants are detected.

7. The method of claim 1 wherein gaseous pollutants are detected using a short-range LIDAR 8. The method of claim 1 wherein environmental pollutants are detected by Raman spectrum using an array of Raman cells connected to a central location by optical fibers.

9. A cell for remote in-situ monitoring of compounds in a liquid using Raman spectroscopy
    a tube having a top and a bottom;
    an optical fiber bundle at the top of said tube;
    a leg near the top of the tube for sample outflow;
    a filter at the bottom of the tube;
    a protective cap covering the tube.

10. The cell of claim 9 wherein the tube is mirrored.

11. The cell of claim 9 wherein a tube from the surface of the liquid is connected to the filter and a one way valve blocks backflow out of the filter.

12. The cell of claim 9 wherein the tube is configured so as to coil around a support.

13. The cell of claim 9 wherein a tube is connected to the filter at the bottom of the cell through a one way valve that blocks outflow from the interior of the cell.

14. A cell for remote in-situ monitoring of compounds in a fluid by surface enhanced Raman spectroscopy or surface enhanced resonance Raman spectroscopy comprising:
    a semipermeable glass cylinder having a top end and a bottom end;
    an optical fiber bundle at the top end of the cylinder;
    a glass stopper at the bottom end of the cylinder;
    a metal sol filling the glass cylinder.

15. A cell for remote in-situ monitoring of compounds in a fluid by surface enhanced Raman spectroscopy or surface enhanced resonance Raman spectroscopy comprising:
    a semipermeable glass cylinder having a top and and a bottom end;
    and a metal electrode sealed at the bottom of the cell.

16. A cell for remote in-situ monitoring of compounds in a fluid by surface enhanced Raman spectroscopy or surface enhanced resonance Raman spectroscopy comprising:
    a nonpermeable glass cylinder having a top and bottom;
    a one-way valve for entrance of liquids into the cell at the bottom of the cylinder;

a filter located at the valve at the bottom of the cylinder;

an outlet at the top of the cell; and a tube connecting the outlet with remote instrumentation.

17. A cell for remote in-situ monitoring of compounds in a fluid by surface enhanced resonance Raman spectroscopy wherein:

the body of the cell is an electrochemically prepared electrode;

the cell is in the shape of a cylinder having a top and bottom, and interior surface and an exterior surface;

the interior surface of the cylinder comprises a conducting material;

a plurality of small diameter tubes are located inside the cylinder, said tubes being made of electrochemically prepared metal in electrical contact with each other and the interior surface of the cylinder;

a one-way entrance valve with detachable filter is located at the bottom end of the cylinder;

an outlet at the top end of the cylinder is adapted and constructed so as to be connected with remote instrumentation; and said cell is sealed to an optical fiber or optical fiber bundle.

* * * * *